(12) United States Patent
Kalofolias

(10) Patent No.: US 10,543,315 B2
(45) Date of Patent: Jan. 28, 2020

(54) MULTI-CHAMBERED VESSELS

(71) Applicant: CUBE PHARMACEUTICALS N.KALOFOLIAS & CO.OE, Athens (GR)

(72) Inventor: Evagelos Kalofolias, Marousi (GR)

(73) Assignee: Cube Pharmaceuticals N. Kalofolias & Co. OE, Athens (GR)

( * ) Notice: Subject to any disclaimer, the term of this patent is extended or adjusted under 35 U.S.C. 154(b) by 170 days.

(21) Appl. No.: 15/680,253

(22) Filed: Aug. 18, 2017

(65) Prior Publication Data

US 2018/0064874 A1 Mar. 8, 2018

Related U.S. Application Data

(63) Continuation of application No. PCT/EP2016/053467, filed on Feb. 18, 2016.

(30) Foreign Application Priority Data

Feb. 19, 2015 (GR) .............................. 20150100066

(51) Int. Cl.
*A61M 5/19* (2006.01)
*A61M 5/315* (2006.01)
(Continued)

(52) U.S. Cl.
CPC .............. *A61M 5/19* (2013.01); *A61J 1/2093* (2013.01); *A61M 5/31511* (2013.01);
(Continued)

(58) Field of Classification Search
CPC .. A61M 5/19; A61M 5/31596; A61M 5/3294; A61M 5/16827; A61M 5/2066; A61M 5/2488; A61M 5/284; A61J 1/2093
See application file for complete search history.

(56) References Cited

U.S. PATENT DOCUMENTS 2,841,145 A * 7/1958 Epps ..................... A61M 5/284
604/89
4,808,006 A * 2/1989 Kaufeler ............. B01F 15/0205
206/219
(Continued)

FOREIGN PATENT DOCUMENTS

CN 102861369 A 1/2013
EP 1213036 A1 12/2002
(Continued)

*Primary Examiner* — Nilay J Shah
(74) *Attorney, Agent, or Firm* — Elmore Patent Law Group, P.C.; Mahreen Hoda; Carolyn Elmore

(57) ABSTRACT

Described are multi-chambered vessels comprising a first chamber, a second chamber, and a seal comprising a first member and a second member, wherein the first and second members are engageable with one another to form a barrier separating the first and second chambers. The first and second members are disengageable from one another to open a channel between the first chamber and second chambers. The vessels allow communication between the first and second chambers at a desired time, for example in order to contact components contained within the chambers or in order to sequentially release components or doses of components from the vessel. Also provided is a kit comprising a seal of the invention. The kit allows a single-chambered vessel to be converted into a multi-chambered vessel capable of controlling communication between the chambers at the final stage of the filling process.

21 Claims, 3 Drawing Sheets

(51) Int. Cl.
  *A61J 1/20*   (2006.01)
  *A61M 5/168*  (2006.01)
  *A61M 5/32*   (2006.01)
  *A61M 5/28*   (2006.01)
  *A61M 5/20*   (2006.01)
  *A61J 1/22*   (2006.01)
  *A61M 5/00*   (2006.01)

(52) U.S. Cl.
  CPC ............ *A61M 5/31596* (2013.01); *A61J 1/22* (2013.01); *A61M 5/002* (2013.01); *A61M 5/16827* (2013.01); *A61M 5/2066* (2013.01); *A61M 5/284* (2013.01); *A61M 5/3294* (2013.01)

(56) References Cited

U.S. PATENT DOCUMENTS

| | | |
|---|---|---|
| 5,125,892 A | 6/1992 | Drudik |
| 5,630,800 A * | 5/1997 | Blank ............... A61M 5/31596 604/228 |
| 6,602,223 B2 * | 8/2003 | Szapiro ................ A61M 5/284 604/82 |
| 2009/0062740 A1 | 3/2009 | Thorne |
| 2012/0265171 A1 | 10/2012 | Thorne et al. |
| 2014/0163465 A1 | 6/2014 | Bartlett et al. |
| 2018/0333331 A1 | 11/2018 | Kalofolias |

FOREIGN PATENT DOCUMENTS

| | | | |
|---|---|---|---|
| WO | 2014004695 A1 | 1/2014 | |
| WO | WO-2014004695 A1 * | 1/2014 | ............ A61J 1/2093 |
| WO | 2015031677 A1 | 3/2015 | |

* cited by examiner

MULTI-CHAMBERED VESSELS

RELATED APPLICATIONS

This application is a continuation of International Application No. PCT/EP2016/053467, which designated the United States and was filed on Feb. 18, 2016, published in English.

This application claims priority under 35 U.S.C. § 119 or 365 to Greece, Application No. 20150100066, filed Feb. 19, 2015. The entire teachings of the above application(s) are incorporated herein by reference.

FIELD

The present invention relates to a multi-chambered vessel, for example a dual-chambered syringe, a kit, a method of converting a vessel having a first chamber into a vessel having a first chamber and a second chamber, a method for contacting components contained in separate chambers of a multi-chambered vessel, and a method of dispensing multiple components or multiple doses of one or more components from a multi-chambered vessel.

BACKGROUND

In recent years, the popularity of lyophilised drugs has risen and has been accompanied by the development of prefilled syringes, pre-filled dual-chambered syringes and dual chambered cartridges for their administration. This has been driven by the market's need for means to facilitate reconstitution of such drugs, increase dose accuracy, avoid dosing and reconstitution mistakes, and improve patient safety and compliance, particularly in the case of self-administered products.

As no filling, measuring or mixing outside the syringe is required by a user, such syringes are convenient and safe to use and allow rapid administration of drugs, making them ideal for self-administration.

Such prefilled syringes/cartridges typically contain a measured dose of a lyophilised drug, in a first chamber, and a diluent in a second chamber. The two chambers are separated by a movable seal. The diameter of the seal is equal to the internal diameter of the second chamber. On application of pressure to a plunger, the seal is forced longitudinally through the second chamber until it reaches a bulge in the wall of the syringe. The diameter of the seal is less than the diameter of the bulged portion of the syringe such that, when the seal reaches the bulged portion, a channel is formed between the seal and the wall allowing diluent to bypass the seal and enter the first chamber to contact the drug. The drug can then be dissolved in the diluent and administered in the normal manner.

It would be desirable to provide an alternative vessel that can control communication between a first chamber and a second chamber that does not require a bulged wall portion. This is because forming the bulged wall adds complexity to the manufacturing process and may affect the structural integrity of the vessel. It would also be advantageous to be able to convert a regular syringe into a dual-chambered syringe which can control communication between the two chambers. A further problem associated with existing dual chambered syringes is the opportunity for components to become trapped in the bypass portion of the device and/or flow back into the first chamber once mixed. This may require the user to further manipulate the device (e.g. angle) in order to ensure that the components are properly combined and that the full dose is administered, which is inconvenient. It would also be advantageous to be able to convert a regular syringe into a dual-chambered syringe which can control communication between the two chambers.

An alternative approach to a dual-chambered vessel capable of keeping components separate until a desired time are dispenser caps of the type used in the health, cosmetics, nutrition and beverage industries as well as in the sports drinks field. An example of a cap used in the sports drink field is available from Vicap Systems EMEA Ltd, Switzerland. A first component is contained in a specialised bottle cap comprising a closure system. The closure system includes a barrier separating the first component from the contents of a bottle to which the cap is fitted, and a puncture device. The puncture device can be operated to puncture the barrier allowing delivery of the first component into the bottle. Further details can be found at the following URL: www.vicapsystems.eu/products/caps/. Another example of a dispenser cap is a Biphase Cap available from Bormioli Rocco S.p.A., Italy. Further details can be found at the following URL: www.bormioliroccopackaging.com/en/pharma/single-dose/traditional/traditional/biphase-kit.html.

Problems with the dispenser cap approach are that the capacity and dimensions of the caps are restricted by the dimensions of the bottle or vial (particularly the neck) to which the cap is fitted, which are typically a standard size or very market/cost needs oriented. The dispenser cap is also restricted by the way in which standard caps are designed to engage the neck of standard bottles or vials (screw neck, crimp neck). The cap is also limited in terms of providing a stable environment for components because of the chemical structure (material) of the cap, the number of parts used for creating the cap and the sealing process in general, which make it difficult to achieve a hermetically sealed environment.

SUMMARY OF THE INVENTION

In a first aspect, the invention provides a multi-chambered vessel comprising a first chamber, a second chamber and a seal comprising a first member and a second member, wherein the first member and the second member are engageable with one another to form a barrier separating the first chamber and the second chamber, the vessel further comprising an actuator configured to cause the first member and the second member to disengage one another to open a channel between the first chamber and the second chamber.

Such a multi-chambered vessel is useful for keeping two (or more) components separate from one another until a time when the components are to be contacted. This is particularly advantageous where the combination of components is, for example unstable or liable to precipitation or sedimentation over longer periods of time. In the case of food products and beverages for example, the vessel ensures freshness and/or stability of components. Moreover, the vessel allows a user to contact components quickly and safely and ensures error free administration and high dose accuracy because there is no bypass region or similar area in which components can become trapped. The vessel of the invention is configured to allow a user to contact the components at a desired time without having to remove the components from the vessel. This eliminates the possibility of contamination of the components or the user during contacting or mixing of the components.

The first member and the second member may have a first position in which the first member and second member are engaged to form a seal separating the first chamber from the second chamber, and a second position in which the first member and the second member are disengaged from one another so that a channel is opened between the first chamber and the second chamber. The channel may provide for liquid communication between the first chamber and the second chamber.

When the first member and the second member are engaged, the seal provides a barrier separating any components contained within the first and second chambers. The seal is preferably impermeable to liquids and/or gases. When a user wishes to provide communication between the first and second chambers, for example to contact the components with one another, the user can actuate the actuator. This causes the first member and the second member to disengage one another which causes a channel between the first chamber and the second chamber to open.

In certain embodiments, the first member is movable and the second member is not movable. In other embodiments, the second member is movable and the first member is not movable. In other embodiments, both the first member and the second member are movable. In embodiments where one of the members is movable, actuation of the actuator causes one of the members to move away from the other member to open the channel. If both members are movable, actuation of the actuator may cause each member to move in opposing directions to open the channel. The movable member or movable members may be movable along a longitudinal axis of the vessel.

The vessel is also useful for dispensing multiple components or aliquots/doses of components from the vessel at desired intervals. This is described below with reference to two different components, but it will be appreciated that equally, two (or more) doses of the same component could be dispensed using the vessel. It will also be appreciated that a vessel of the invention may comprise more than one seal as defined herein and therefore more than two components or doses could be dispensed in accordance with the general method described below. In such embodiments, the opening of the channel does not necessarily result in contacting components contained within separate chambers. Instead, prior to disengagement of the first member and the second member, a first component in a first chamber may be dispensed from the vessel via an outlet, for example by moving the actuator to a first position. Subsequently, the actuator may be actuated e.g. moved to a second position, causing the first member and the second member to disengage, thereby opening a channel between the first chamber and the second chamber. A second component in a second chamber can then enter the first chamber via the channel. Finally, the second component may be dispensed from the vessel via the outlet, for example by moving the actuator to a third position. The first and third positions may be the same position. For example, the actuator may be a piston and plunging the piston into a chamber of the vessel may facilitate dispensing of components and withdrawing the piston (partially or fully) may facilitate disengagement of the first member and the second member. Variations on this embodiment for delivering components in different doses/aliquots and/or in different orders will be apparent to the skilled person.

The shape and/or size of the first member and the second member can be adjusted based on various factors including, for example, the size and shape of the vessel, the desired flow rate between chambers and the desired resistance of the members to movement and/or disengagement. The vessel may comprise an outlet. The first member may be positioned closer to the outlet than the second member or vice versa. In an embodiment, the second member comprises a plug and the first member comprises a seal portion and a through hole, the through hole being configured to receive at least a portion of the plug when the first member and the second member are engaged. When the plug is removed from the through hole upon disengagement of the first and second members, communication between the first and second chambers is provided via the through hole. In other words, the through hole may provide the channel between the first chamber and the second chamber. The plug and the through hole can be any shape or size.

The cross sectional area of the through hole and/or the cross sectional area of the plug may not be constant along their respective lengths. For example, the through hole may comprise a first portion and a second portion, the second portion being narrower i.e. having a smaller cross section than the first portion. The cross sectional area of the second portion of the through hole may be from about 5% to about 95% of the cross sectional area of the first portion of the through hole, for example about 90%, about 80%, about 70%, about 60%, about 50%, about 40%, about 30%, about 20%, or about 10%. Alternatively or additionally, the plug may comprise a first portion and a second portion, the first portion being narrower i.e. having a smaller cross section than the second portion. The cross sectional area of the first portion of the plug may be from about 5% to about 95% of the cross sectional area of the second portion of the plug, for example about 90%, about 80%, about 70%, about 60%, about 50%, about 40%, about 30%, about 20%, or about 10%.

The first and second portions of the through hole may or may not be equal in length. For example, the second portion of the through hole may be shorter in length than the first portion of the through hole. The first and second portions of the plug may or may not be equal in length. For example, the second portion of the plug may be shorter in length than the first portion of the plug. The first portion of the plug may be capable of being at least partially received within the first portion of the through hole, and may be fully received within the first portion of the through hole. The first portion of the plug may not be capable of being received within the second portion of the through hole. The second portion of the plug may not be capable of being received within the first portion of the through hole. An advantage of such an arrangement is that when the first and second members are fully engaged, a "double seal" is achieved i.e. the first portion of the plug seals against the second portion of the through hole and the second portion of the plug seals the first portion of the through hole. This will be described with reference to diameter, although it will be appreciated that the through hole does not have to be circular in cross section.

In one embodiment, the through hole comprises a first portion having a first diameter and a second portion having a second diameter, wherein the second diameter is less than the first diameter. For example, the second diameter may be from about 5% to about 95% of the first diameter, for example about 90%, about 80%, about 70%, about 60%, about 50%, about 40%, about 30%, about 20%, or about 10%. To achieve this, the first member may, for example, be formed from two components, each component having a through hole of different dimensions. The diameter of the first portion of the through hole may be sufficient to accommodate at least a portion of the plug of the second member. The diameter of the second portion of the through hole may be small enough to prevent the plug entering the second portion of the through hole, such that when the first and second members are engaged, the end of the plug seals the opening of the narrower portion of the through hole. In one embodiment, the plug of the second member comprises a first portion having a diameter less than or equal to, for example substantially the same as, the diameter of the first portion of the through hole such that the first portion of the through hole can accommodate the first portion of the plug. The plug may have a second portion having a diameter greater than the diameter of the first portion of the plug and greater than the diameter of the first portion of the through hole, such that the second portion of the plug cannot enter the first portion of the through hole and creates a seal against an outer portion of the first member when the first member and the second member are fully engaged.

The shape and/or size of the through hole can influence the rate at which a component contained within one of the chambers can pass into the other chamber. For example, if a higher rate of transfer between chambers is desired, a larger through hole may be provided. Similarly, more viscous fluids may require the use of larger through holes to obtain the same rate of transfer as less viscous fluids. The skilled person can adjust the size and/or shape of the through hole accordingly. The plug may comprise an exposed portion that is not received within the through hole when the first member and the second member are engaged. The exposed portion may be generally conical in shape. This helps to direct fluid flow away from the plug and reduce the resistance of the second member to fluid pressure. In other embodiments, the plug is fully received within the through hole and so does not comprise an exposed portion.

The second member may comprise a support structure configured to engage an internal wall of the vessel, either directly or indirectly, and hold the plug in position relative to the through hole in the first member. In an embodiment, the support structure comprises a generally annular member configured to engage the internal wall of the vessel, either directly or indirectly. For example, an insert such as a tube or tunnel may be provided within the vessel such that support structure engages the insert rather than the vessel wall itself. An annular member may be preferred if the vessel has a generally cylindrical shape. The support structure may further comprise one or more radial members extending between the annular member and the plug such that one or more openings are defined in the support structure between the annular member and the plug. In this embodiment, the openings are preferably configured to align with the seal portion of the first member when the first and second members are engaged. In one embodiment, the support structure comprises a support member spanning the internal diameter of the annular member. Preferably, this support member bisects the annular member such that two openings of equal size are present in the annular member.

The use of radial members (or similar) and the presence of openings minimises the surface area of the second member and allows a fluid e.g. a liquid, gas or a combination thereof, or in some cases a solid such as a gel or a powder, to pass through the second member and act on the seal portion of the first member. Thus, the configuration means that the second member provides lower resistance to pressure than the first member. The first member may provide a greater resistance to pressure than the second member due to the presence of the seal portion. The force of the solid or fluid acting on the seal portion may cause the first member to move away from and disengage the second member. A benefit of the reduced resistance of the second member to pressure, is that the second member preferably either does not move in response to the action of the solid or fluid or moves to a lesser extent than the first member. The amount of structural support and the resistance required may be a factor in determining the most suitable number and shape of radial members and the size of the openings in the support structure.

The first member and the second member may each have a surface which contacts an internal wall of the vessel. The surface area of the internal wall-contacting surface of the second member may be different to the surface area of the internal wall-contacting surface of the first member. For example, the second member may have a greater surface area in contact with the internal wall than the first member. An advantageous effect of such a configuration is that the second member generates more friction against the internal wall than the first member, meaning that the first member moves along a longitudinal axis of the vessel in response to actuation of the actuator in preference to the second member. If it is desirable instead for the second member to move in preference to the first member, the first member may be provided with an internal wall-contacting surface having a greater area than that of the second member. The surface area in contact with an internal wall of the vessel can be adjusted by for example, adjusting the length of the member and/or by providing the member with ridges (thereby reducing the surface area in contact with the vessel wall).

The actuator may or may not contact the seal directly in order to cause disengagement of the first and second members. If the actuator does not contact the seal directly, a mechanical linkage may be provided between the actuator and one or both of the first and second members. Alternatively, the actuator may cause the first member and the second member to disengage by exerting pressure on the seal in the manner of a piston.

In an embodiment, the actuator comprises a piston. The piston may be at least partially received within the first or second chamber of the vessel. A piston may be a preferred if the chamber contains a fluid i.e. a liquid or a gas or a combination of liquid and gas. In such embodiments, the second member may be provided between the first member and the piston when the first and second members are engaged. The piston may be configured to cause the first member and the second member to disengage by exerting pressure on a piston-facing surface of the first member sufficient to move the first member along a longitudinal axis of the vessel. The piston-facing surface of the first member may have a surface area that is greater than a piston-facing surface area of the second member, such that the first member has a greater resistance to pressure exerted by the piston than the resistance of the second member to pressure exerted by the piston. For example, the seal portion of the first member may be the piston facing surface or a portion thereof.

Thus, the piston may be configured to cause the first member and the second member to disengage when it is plunged into a chamber thereby increasing pressure within the chamber and "pushing" the first member away from the second member or vice versa as described above. Alternatively or additionally, the piston may be configured to cause the first member and the second member to disengage when it is withdrawn from a chamber, by reducing the pressure within a chamber and "pulling" the first member away from the second member or vice versa. In such embodiments, the first member may be provided between the second member and the piston when the first and second members are engaged.

In one embodiment the actuator is in the form of a cap which fits to the vessel. The cap may form a closure covering an opening at one end of the vessel (for example a screw cap or push-fit cap). The cap may comprise a depressible elastic portion. The elastic portion may be configured to increase the pressure within a chamber of the device when actuated to cause disengagement of the first and second members. Actuation of the elastic portion may involve pushing the elastic portion towards the opening of the vessel. The elastic portion may at least partially enter the vessel upon actuation. Alternatively, a mechanical linkage between the elastic portion and the seal may be provided to link the depression of the elastic portion to movement of the first and/or second member.

In certain embodiments, the actuator is configured to cause the first member and the second member to re-engage once the necessary transfer of a component or components has taken place thereby closing the channel and preventing backflow.

In some embodiments, the vessel is generally cylindrical in shape. In other embodiments, the vessel has a generally rectangular cross section. The vessel may comprise an outlet for dispensing a component, especially a liquid, therefrom. For example, the vessel may be a syringe, preferably a dual-chambered syringe, wherein the two chambers are separated by the seal of the invention. The syringe may or may not be provided with a, needle. In another embodiment, the vessel is a multi-chambered food product or beverage container, for example a bottle. The vessel may comprise any known bottle cap or closure, for example one that allows a user to drink from the bottle or otherwise dispense one or more components from the bottle. The vessel may be a cartridge for delivering a cosmetic or a domestic or industrial chemical such as an adhesive or sealant. Any known vessel that is not already provided with a seal defining a first chamber and a second chamber may be provided with a suitable seal in order to practice the present invention.

The first and second members of the seal are preferably made from a material that is chemically inert so that they have no impact on any components contained within the vessel. For example, the first and/or second members could be made from the same material as the vessel. Examples of suitable materials include Polyethylene terephthalate (PET), Polypropylene (PP), Thermoplastic elastomers (TPE), HDPE, LLDPE, LDPE, cyclopoly olefin resin, cyclo olefin copolymer, glass, titanium and aluminium. In choosing the material, one or more of the following factors may be taken into consideration: physicochemical characteristics/properties of the vessel, purpose of the vessel, physicochemical characteristics/properties of the component/s, storage conditions, scope of use and/or way of use etc. The first member and the second member may be made from the same material or different materials. The amount of friction between the first member and the second member may influence the force necessary to cause disengagement of the two members. Therefore, adjusting the friction between the two members is one way to influence the force necessary to cause disengagement of the two members.

The multi-chambered vessel may contain or be suitable for containing a solid component and/or a liquid component in one or more of its chambers. In one embodiment, the first chamber contains or is suitable for containing a first component and the second chamber contains or is suitable for containing a second component. The first component may be a liquid component or a solid component. The second component may be a liquid or a solid component. In an embodiment, the first chamber contains or is suitable for containing a solid component and the second chamber contains or is suitable for containing a liquid component. In another embodiment, both the first and second chambers contain or are suitable for containing liquid components. In another embodiment, both the first and second chambers contain or are suitable for containing solid components. The terms "solid" and "liquid" should be considered to include, for example, gels, foams and powders. The term "solid" includes semi-solid substances. The term "contains" does not necessarily exclude the presence of other substances within each chamber. For example, a chamber containing a solid component, may also contain gas and/or a liquid. A chamber containing a liquid component may also contain a solid and/or a gas. Contacting or mixing of the first component and the second component may lead to the formation of, for example, a suspension, a dispersion, a solution, an emulsion or a mixture. A liquid component may or may not be a solvent or diluent suitable for reconstituting or dissolving a solid component.

One or both of the first and second components may comprise a pharmaceutical agent or may be a pharmaceutical formulation. Alternatively, one or both of the first and second components may be a non-pharmaceutical formulation. A pharmaceutical formulation or a non-pharmaceutical formulation may be formed once the components have been contacted. Pharmaceutical formulations/agents may contain any active pharmaceutical ingredient or a combination of ingredients and may be in any form. For example, a pharmaceutical formulation may be lyophilised, non-lyophilised, microencapsulated, nanoencapsulated, freeze dried, and/or may be provided as a tablet, gel, capsule, powder, paste, cream, ointment or solution.

Pharmaceutical formulations/agents may be characterised as, for example, biopharmaceuticals, biologicals, biomaterials, vaccines, peptides, small molecules, antibodies, hormones, corticosteroids, anti-inflammatories, antihistamines, antibiotics, anticoagulants, glycosaminoglycans, polysaccharides etc.

Non pharmaceutical formulations/agents may contain any ingredient or a combination of ingredients and may be lyophilised, non-lyophilised, microencapsulated, nanoencapsulated, freeze dried, and/or may be provided as a tablet, gel, capsule, powder, paste, cream, ointment, or solution.

Non pharmaceutical formulations/agents may be characterised as, for example, nutrition and/or health products, food products, beverages, food supplements, cosmetics or any other industrial or domestic chemical e.g. adhesives, sealants, glues, fertilisers, pesticides, fungicides, herbicides, miticides. Food products, beverages and supplements may comprise or consist essentially of one or more sugars such as glucose or dextrose, a stimulant such as caffeine or taurine, one or more proteins such as whey protein, carbohydrates, complex carbohydrates, resistant carbohydrates, monosaccharide, oligosaccharides, polysaccharides, one or more vitamins, minerals, micronutrients, an iron supplement or combinations thereof. Examples include energy tablets, protein supplements, vitamin supplements, PUFAs, LCPUFAs, MUFAs, SCPUFA, essential oils, flavouring agents, sweetening agents.

Any of the chambers may be treated to minimise or exclude air/oxygen once a component or components have been introduced into the chamber, for example by flushing the chambers with nitrogen or carbon dioxide.

The first component or a portion thereof and/or the second component or a portion thereof can move through the channel formed by disengagement of the first member and the second member. In certain embodiments, this allows the first and second components to contact one another. In one embodiment, the vessel is configured to permit movement in a single direction through the channel. For example, a pressure gradient may ensure that components can move through the channel in only a single direction. A pressure gradient may be created by a user actuating the actuator, for example if the actuator is a piston. In some embodiments, the physical properties of the components may prevent one of the components moving through the channel. For example, where a first component is a liquid and a second component is a solid, the liquid may be able to pass through the channel whereas the solid may be confined to its starting chamber due to its size or conformation. However, in some embodiments, the solid component is capable of moving through the channel. This may be the case if the solid component is in the form of, for example, a gel or a powder. In some embodiments, the entire second component is able to move into first chamber via the channel. In other embodiments, the entire first component is able to move into the second chamber via the channel.

The multi-chambered vessel may comprise more than two chambers. In such embodiments, further seals as defined herein may be provided to define additional chambers. For example, three chambers can be defined using two seals, four chambers can be defined using three seals, five chambers can be defined using four seals etc. The actuator may be configured to cause disengagement of the first and second members of each seal either simultaneously or at different times. Preferably, disengagement of each set of first and second members does not occur simultaneously. This allows a user to control movement of components through chambers in a sequential manner. For example, it may be desirable to contact a first component initially contained in a first chamber with a second component initially contained in a second chamber for a period of time before contacting that mixture of first and second components with a third component contained within a third chamber. This can be achieved by disengaging first and second members of a first seal separating the first and second chambers and subsequently disengaging first and second members of a second seal separating the second and third chambers.

In a second aspect, the invention provides a kit comprising an accessory for a vessel, the accessory comprising a seal comprising a first member and a second member as defined herein. The kit may further comprise a vessel, for example a vessel as described herein.

The kit may be used to convert a single chambered vessel (for example a syringe or a bottle) into a dual-chambered vessel suitable for containing a first component separately from a second component and contacting the components at a desired time or dispensing the components individually from the vessel at desired intervals. If the starting vessel has more than one chamber already, such a kit can be used to add an additional chamber to the vessel. Communication between the new chamber and one of the exiting chambers can be controlled using the interaction between the first member and the second member as described herein. The kit may further comprise securing means for securing the first member or the second member to an internal wall of the vessel. The securing means may be an adhesive. The vessel wall may comprise a slot or groove into which at least a portion of either the first or second member can be inserted. For example, the first or second member may comprise an annular member configured to engage a corresponding groove running around an internal circumference of the vessel. The annular member may form part of the support structure of the second member described herein. Other means for securing the first member or the second member in position will be apparent to the skilled person and are within the scope of the invention. For example, the securing means may comprise a structure which engages an end wall of the vessel or blocking means within the vessel.

In a third aspect, the invention provides a method of converting a vessel having a first chamber (for example a syringe or a bottle) into a vessel having a first chamber and a second chamber, the converted vessel being capable of controlling communication between the first chamber and the second chamber, the method comprising inserting a seal as defined herein into a vessel having a first chamber to define within the vessel a first chamber and a second chamber. The vessel may of course comprise additional chambers. The seal may be any seal described herein. The method may further comprise loading a first component into the first chamber and a second component into the second chamber. The first and second components may be as defined in relation to the first aspect of the invention. The vessel may comprise an actuator as described herein. The vessel may be any vessel described herein. The method may include reducing the levels of or excluding air/oxygen from one or more of the chambers using any of the methods described herein.

Thus, the invention allows a standard vessel (e.g. a simple syringe or bottle) obtained from any supplier to be converted into a multi-chambered vessel with the ability to control communication between the chambers. The invention will therefore be particularly useful for packaging companies and the like who are involved in the filling of vessels because modification of the standard vessel can take place even at the final stage of the manufacturing/packaging process in conjunction with filling of the vessel.

In a fourth aspect, the invention provides a method of contacting a first component contained within a first chamber of a multi-chambered vessel with a second component contained within a second chamber of the vessel and separated from the first component by a seal as defined herein, the method comprising disengaging the first member and the second member thereby opening a channel between the first chamber and the second chamber such that the first component and the second component can contact one another.

The vessel, seal and components may be as described in relation to any other aspect of the invention. Preferably the first member and the second member are disengaged by actuating an actuator as described in relation to the first aspect of the invention.

In a fifth aspect, the invention provides a method of dispensing multiple components or multiple doses of one or more components from a multi-chambered vessel wherein a first component or first dose is contained within a first chamber of a multi-chambered vessel and a second component or a second dose is contained in a second chamber of the vessel, the first component or first dose being separated from the second component or second dose by a seal comprising a first member and a second member, wherein the first member and the second member are engageable with one another to form a barrier separating the first chamber and the second chamber, the method comprising:
  (i) dispensing the first component or first dose from the vessel via an outlet.
  (ii) causing the first member and the second member to disengage one another to open a channel between the first chamber and the second chamber and allowing the second component or second dose to enter the first chamber via the channel.
  (iv) dispensing the second component or second dose from the vessel via an outlet.

The vessel, seal and components may be as described in relation to any other aspect of the invention. Preferably the first member and the second member are disengaged by actuating an actuator as described herein. Dispensing of the components or doses via the outlet may or may not be linked to actuation of the actuator. For example, if the actuator is a piston, plunging of the piston into a chamber of the device may force a component or dose thereof out of the device via an outlet. Alternatively, a component or dose thereof may be dispensed simply by tipping or pouring the component out of the device via the outlet. This may be appropriate, if for example the vessel is a bottle, wherein the outlet is the opening of the bottle.

The outlet from which the first component is dispensed may or may not be the same outlet from which the second component is dispensed. The method according to the fifth aspect may be combined with one or more steps of the method according to the fourth aspect of the invention. In this way, a first component and a second component (for example) may be contacted with one another, and subsequently one or more doses of the combined components may be dispensed from the vessel. This may be preceded or followed by the dispensing of a different component or combination of components (which may be contained in a separate chamber) from the vessel.

Preferred features of each aspect of the invention are as for each of the other aspects mutatis mutandis.

FIGURES

FIG. 1A: a side view of an embodiment of a multi-chambered vessel.

FIG. 1B: side, front and rear views of an embodiment of a seal comprising a first member and a second member.

FIG. 2: a schematic illustration showing how components within a dual-chambered vessel can be contacted with one another and dispensed from the vessel.

FIG. 3: cross section of an embodiment of a seal comprising a first member and a second member.

Figure 1A:
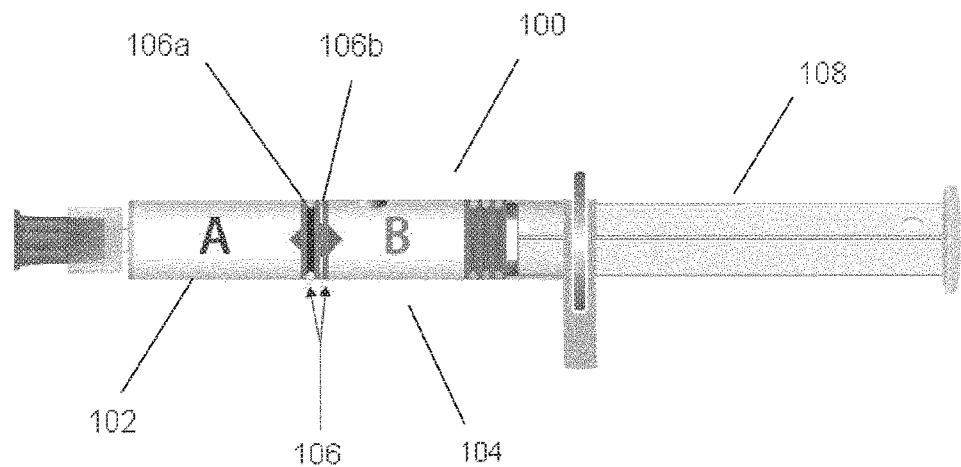
FIG. 1A shows a side view of an embodiment of a multi-chambered vessel 100. In this embodiment, the vessel 100 is a syringe comprising a first chamber 102 and a second chamber 104 separated by a seal 106. The seal 106 comprises a first member 106a and a second member 106b. In the configuration shown in the Figure, the first member 106a and the second member 106b are engaged to form a barrier which prevents a first component, component A and second component, component B from contacting one another. In this embodiment, component B is a fluid. An actuator in the form of a plunger 108 is provided and is configured to cause the first member 106a and the second member 106b to disengage when the plunger 108 is urged into the second chamber 104.
Figure 1B:
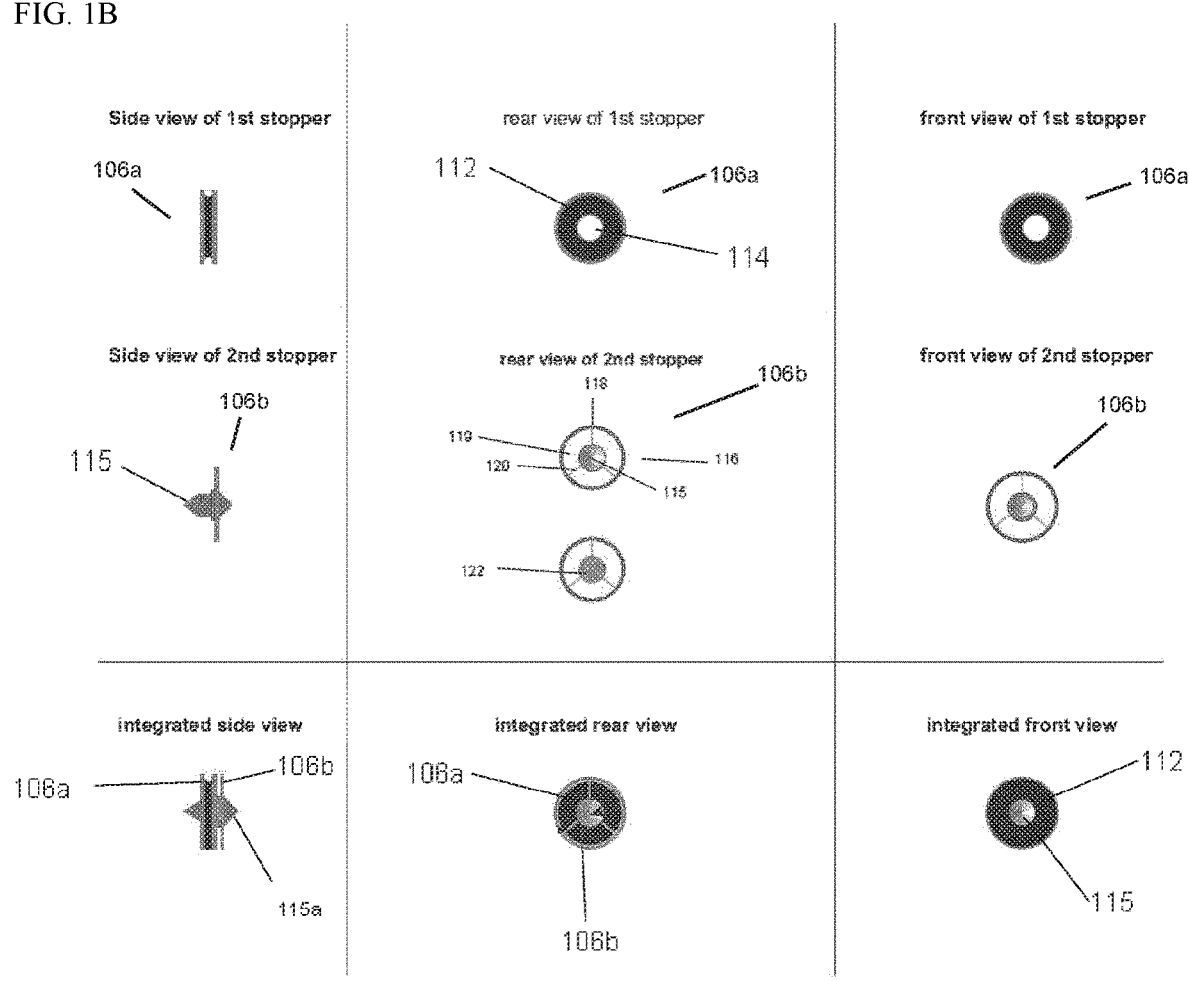
FIG. 1B shows side, rear and front views of the first and second members 106a and 106b of FIG. 1A, both in isolation and in an integrated configuration. The first member 106a comprises a seal portion 112 and a through hole 114. The second member comprises a plug 115 and a support structure 116. The plug 115 is configured to plug the through hole 114 in the first member 106a when the first member 106a and the second member 106b are engaged. The support structure 116 comprises an annular member 118 that is configured to engage an internal wall of the vessel 100 to hold the second member 106b in the correct position relative to the vessel 100 and the first member 106a. The support structure 116 also comprises three radial members 120 which extend between the annular member 118 and the plug 115. The radial members 120 define openings 119 between the annular member 118 and the plug 115. The configuration of the support structure 116 is such that the surface area of the second member 106b is low relative to the surface area of the first member 106a. The support structure 116 provides a much lower resistance to pressure exerted by the plunger 108 than the resistance provided by the seal portion 112 of the first member 106a. This means that, upon actuation of the plunger, the first member 106a is moved along a longitudinal axis of the vessel by pressure in preference to the second member 106b. This causes disengagement of the first and second members. In this embodiment, the second member 106b further comprises a sealing member 122 which provides an extra seal around the plug 115.

It can be seen from the integrated view in FIG. 1B that the plug 115 comprises an exposed portion 115a that is not received within the through hole 114 of the first member 106a when the first member 106a and the second member 106b are engaged. The exposed portion 115a is conical in shape and this helps to direct fluid through a plurality of openings 119 in the second member 106b towards the seal portion 112 of the first member 106a. In the integrated views, in can be seen that the openings 119 in the second member 106b are aligned with the seal portion 112 of the first member 106a allowing a component such as component B to flow through the openings 119 and contact and act upon the seal portion 112 directly.

Figure 2:
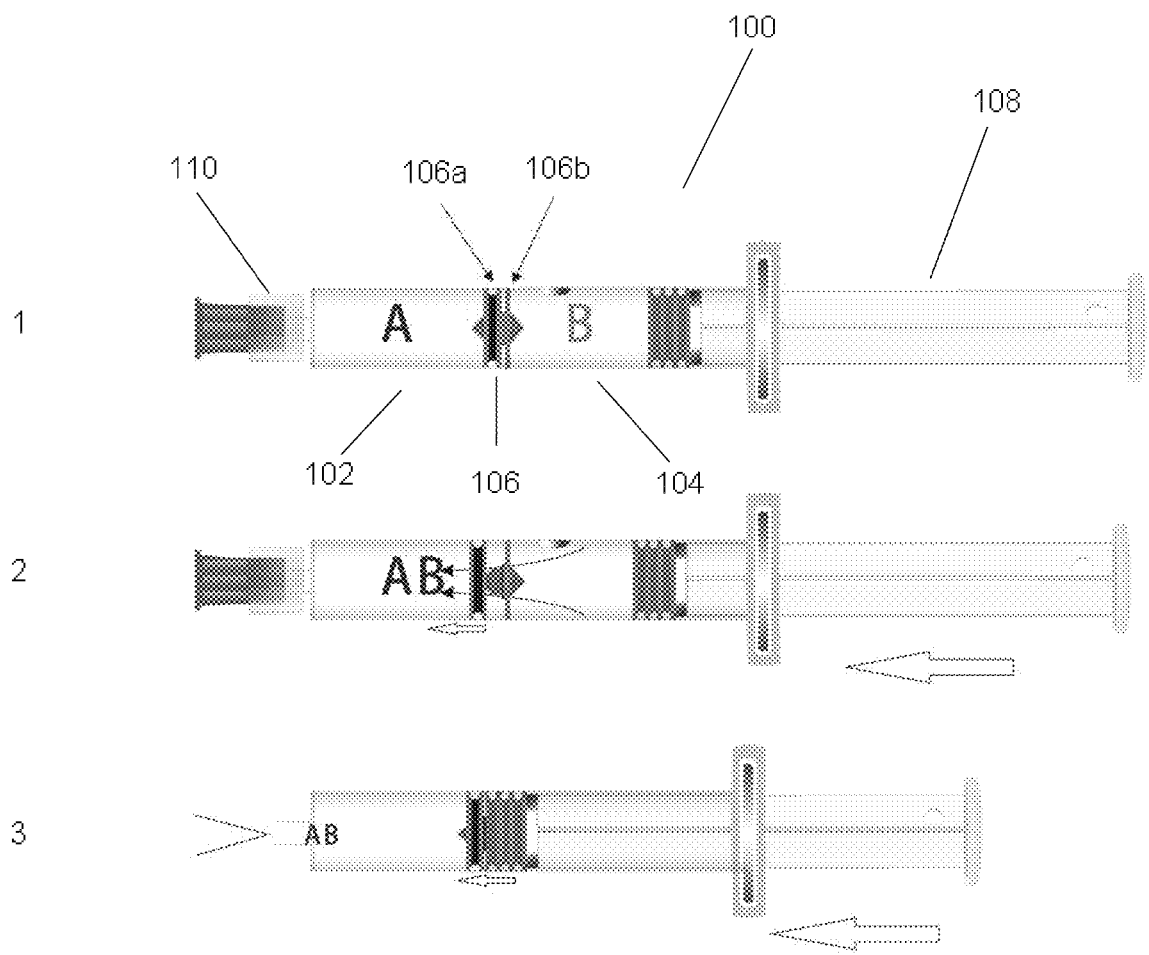

FIG. 2 is a schematic illustration showing operation of the embodiment of a vessel shown in FIG. 1. In step 1, the first member 106a and the second member 106b are engaged meaning that component B in the second chamber 104 and component A in the first chamber 102 cannot contact one another and are confined to their respective chambers. In step 2, the plunger 108 is actuated. This increases the pressure within the second chamber 104 and pushes the first member 106a in a longitudinal direction away from the plunger 108. The second member 106b is not moved by the pressure exerted by the plunger 108 because the piston-facing surface area of the second member 106b is smaller than the piston facing surface area of the first member 106a. Therefore, the first member 106a and the second member 106b disengage. The plug is therefore removed from the through hole in the first member 106a allowing component B to enter the first chamber 102 via the through hole in the first member 106a. Component B also passes through the openings 119 (shown in FIG. 1) in the second member 106b prior to passing into the first chamber via the through hole in the first member 106a. In step 3, the plunger 108 is fully inserted and the combined components A and B are dispensed from the vessel 100 via outlet 110. In this embodiment, the plunger causes the first member 106a and the second member 106b to re-engage once component B has been fully transferred to the first chamber 102. This prevents backflow of components A and B and ensures that the entire volume of components A and B is dispensed via the outlet 110.

Figure 3:
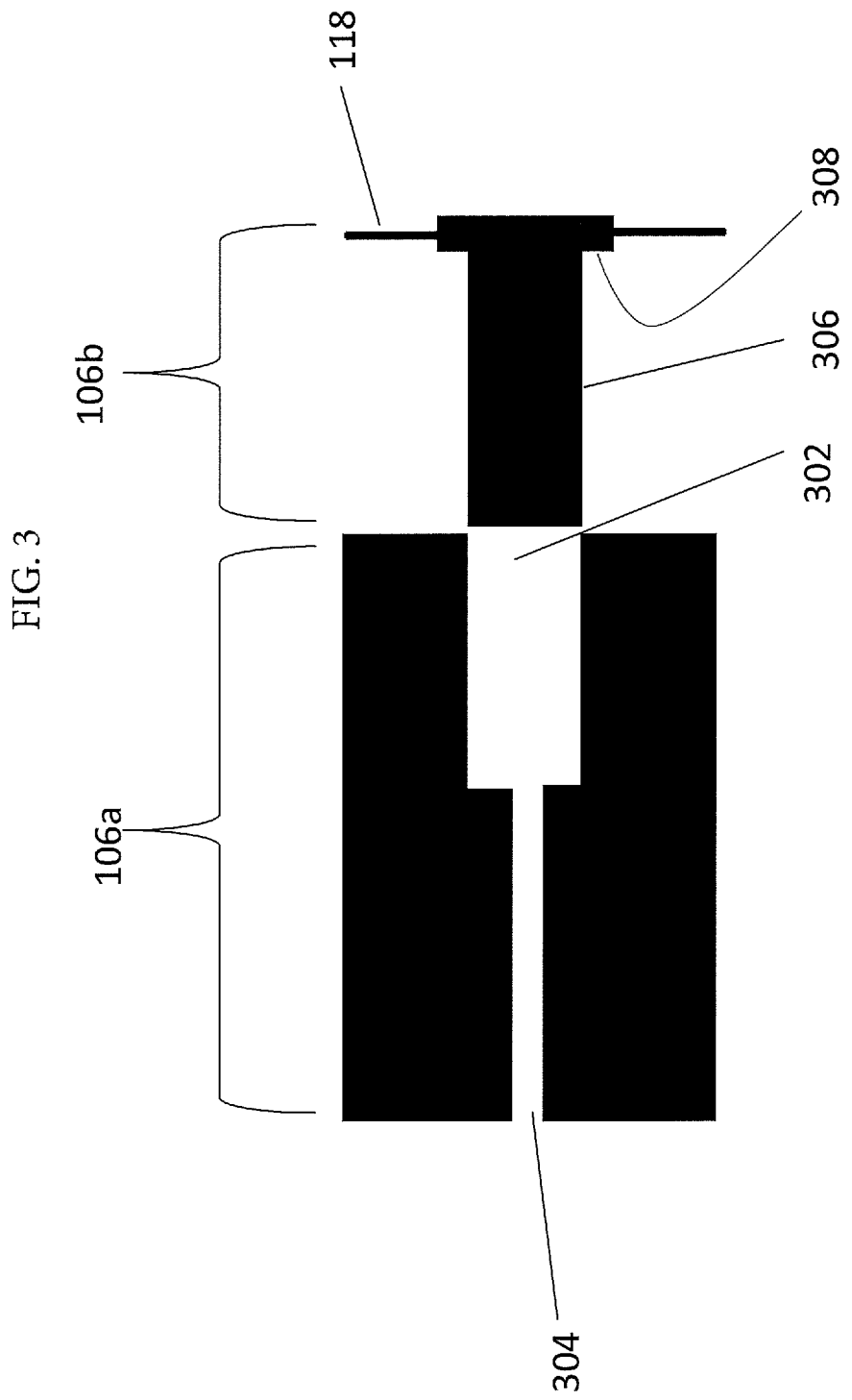

FIG. 3 shows a cross section of an embodiment of a seal of the invention comprising a first member 106a and a second member 106b. The first member has a through hole comprising a first portion 302 and a second portion 304. The diameter of the second portion 304 is smaller than the diameter of the first portion 302. The second member 106b comprises a plug having a first portion 306 and a second portion 308, and an annular support structure member 118.

The diameter of the second portion of the plug 308 is greater than the diameter of the first portion of the plug 306. The dimensions of the first portion of the plug 306 are such that the first portion of the plug is a tight fit within the first portion of the though hole 302. The first portion of the plug 306 is however too large to enter the second portion of the though hole 304 and thus the second portion of the through hole 304 is sealed by an end of the first portion of the plug 306 when the first member 106a and the second member 106b are fully engaged. The second portion of the plug 308 is too large to fit into the first portion of the through hole 302 and therefore creates a second seal against an outer portion of the first member 106a when the first member 106a and the second member 106b are fully engaged.

EXAMPLE 1

A seal comprising a first member and a second member was prepared. The first member (designed to perform the function of the first member 106a of the Figures) was fabricated from the standard seal of a 10 ml syringe plunger. This was modified by inserting the plunger seal of a 5 ml syringe into a recess in the 10 ml seal to reduce the size of the recess. A through hole 4 mm in diameter was made through the centre of the combined seals.

The second member (designed to perform the function of the second member 106b in the Figures) comprised a plug fixed to a support member spanning the 10 mm internal diameter of an annular support structure, such that two openings were present on either side of the support member. The support member had thickness of 1 mm and a length of 15 mm which was equal to the external diameter of the annular support structure. The plug comprised a first cylindrical portion and a second cylindrical portion. The diameter of the first cylindrical portion was 3.9 mm and the length was 3 mm. The diameter of the second cylindrical portion was 5 mm and the length was 1 mm. The second cylindrical portion was fixed directly to the support member. The first cylindrical portion was able to enter and fit inside the through hole of the first member and the second cylindrical portion was not able to enter the through hole. This configuration resulted in a tight seal once the first member and second member were engaged.

The first member and second member were inserted into a 10.0 ml single use, latex free, pthalates free, ethylene oxide sterilised syringe (SAFETY A.T/G. of Anats Health Products, Greece). The syringe had an inner barrel diameter of 14 mm and comprised a plunger which terminated in a seal. The plunger seal comprised pronounced annular portions, between which were two furrows. The plunger seal had a conical terminus ending and total width (side view) was equal to 7 mm and total diameter was 15 mm.

The first member and the second member were engaged such the plug portion of the second member sealed the through hole of the first member. The second member was closest to the plunger and the first member was closest to the outlet of the syringe. The presence of the seal (combined first and second members) defined two chambers within the syringe which will be referred to as chamber A and chamber B, chamber B being closest to the plunger and chamber A being closest to the syringe's outlet.

In this embodiment, it was important that the first member moved longitudinally through the syringe (away from the plunger) in preference to the second member upon actuation of the plunger, to ensure separation of the first and second members. In this embodiment, this was achieved by using an annular support structure having a smooth surface with no pronounced portions, to maximise the surface area in contact with the syringe wall and hence maximise friction. In contrast, the first member comprised a plurality of annular ridges running circumferentially around its outer surface, thereby minimising the surface area in contact with the syringe wall and hence minimising friction. Such an effect could be achieved in a number of different ways. Another possibility would be to adjust the relative lengths of the first and second members to adjust the surface area of each member that is in contact with the syringe wall.

To test the efficacy seal, the first and second members were fully engaged, the syringe was held vertically (outlet facing upwards) and 1 ml of water was introduced into chamber A. It was confirmed that the seal prevented leakage of water into chamber B. The syringe was inverted and 1 ml of water was introduced into chamber B. It was confirmed that the seal prevented leakage of water into chamber A. This demonstrated that the seal was effective at preventing communication between the chambers in both directions.

The ability of the first and second members to separate following actuation of the plunger to allow water to pass between the chambers was then tested. 1 ml of water was introduced into chamber B (air was not excluded from the chamber), and the syringe was held vertically with the outlet facing upwards such that chamber B comprised a layer of trapped air against the seal (second member) above the 1 ml of water.

The plunger was pushed (upwards) into the syringe and this forced the first member to disengage from the second member enough for the trapped air to pass through into chamber A via the through hole, which was accessible due to the disengagement of the first and second members. Further insertion of the plunger into the syringe caused further disengagement and water was forced into chamber A via the through hole. Once all of the water had passed into chamber A, no further separation of the two members was observed despite continuous movement of the plunger into the syringe. Eventually, the plunger seal engaged the second member and further insertion of the plunger caused the second member to re-engage with the first member. Further insertion of the plunger forced all of the water out of the syringe via the outlet. The test was therefore deemed successful as the first member and second member disengaged upon actuation of the plunger to allow the water in chamber B to pass into chamber A.

EXAMPLE 2

A second experiment was conducted using the syringe and protocol of Example 1 except that water was replaced with a high viscosity liquid component. The selected viscous liquid component was 1.5% sodium hyaluronate in 0.2M sodium chloride with a measured zero shear viscosity of 530 Pas.

Again surprisingly, despite the high viscosity of the component, the test was successful and the sodium hyaluronate solution was able to pass into chamber A via the through hole formed upon disengagement of the first member and the second member. In this experiment, disengagement was observed to be more extensive than in Example 1 and automatically adjusted to the needs of the highly viscous component.

These examples further serve to demonstrate that a single-chambered vessel can be converted into a multi-chambered vessel capable of controlling communication between chambers even at the final stage of the manufacturing process where filling is taking place.

The invention claimed is:

1. A multi-chambered vessel comprising a first chamber (102), a second chamber (104), and a seal (106) comprising a first member (106a) and a second member (106b), wherein the first member (106a) and the second member (106b) are engageable with one another to form a barrier separating the first chamber (102) and the second chamber (104), the multi-chambered vessel further comprising an actuator (108) configured to cause the first member (106a) and the second member (106b) to disengage one another to open a channel between the first chamber (102) and the second chamber (104),
   wherein the second member (106b) comprises a plug (115) and the first member (106a) comprises a seal portion (112) and a through hole (114), the through hole (114) being configured to receive at least a portion of the plug (115) when the first member (106a) and the second member (106b) are engaged, and
   wherein the second member (106b) comprises a support structure (116) configured to engage an internal wall of the multi-chambered vessel and hold the plug (115) in position relative to the through hole (114) of the first member (106a),
   and further wherein the first member (106a) has a greater resistance to pressure exerted in a distal direction via the actuator than the second member (106b).

2. The multi-chambered vessel of claim 1, wherein (i) the first member (106a) is movable and the second member (106b) is not movable, or (ii) both the first member (106a) and the second member (106b) are movable.

3. The multi-chambered vessel of claim 2, wherein the first member or both the first and second members are movable along a longitudinal axis of the multi-chambered vessel.

4. The multi-chambered vessel of claim 1, wherein the plug (115) comprises an exposed portion (115a) that is not received within the through hole (114) when the first member (106a) and the second member (106b) are engaged.

5. The multi-chambered vessel of claim 4, wherein the exposed portion (115a) is conical in shape.

6. The multi-chambered vessel of claim 1, wherein the support structure (116) comprises (i) an annular member (118) configured to engage the internal wall of the multi-chambered vessel, and (ii) one or more radial members (120) extending between the annular member (118) and the plug (115) such that one or more openings (119) are defined between the annular member (118) and the plug (115).

7. The multi-chambered vessel of claim 6, wherein when the first member (106a) and the second member (106b) are engaged, the one or more openings (119) in the second member (106b) align with the seal portion (112) of the first member (106a).

8. The multi-chambered vessel of claim 1, wherein the actuator (108) comprises a piston.

9. The multi-chambered vessel of claim 8, wherein when the first member (106a) and the second member (106b) are engaged, the second member (106b) is situated between the first member (106a) and the piston.

10. The multi-chambered vessel of claim 8, wherein the piston is configured to cause the first member (106a) and the second member (106b) to disengage by exerting pressure on a piston-facing surface of the first member (106a) sufficient to move the first member (106a) along a longitudinal axis of the multi-chambered vessel.

11. The multi-chambered vessel of claim 10, wherein the piston-facing surface of the first member (106a) has a surface area that is greater than a piston-facing surface area of the second member (106b), such that the first member (106a) has the greater resistance to the pressure exerted by the piston that the resistance of the second member (106b) to the pressure exerted by the piston.

12. The multi-chambered vessel of claim 1, comprising a first component contained within the first chamber (102) and a second component contained within the second chamber (104).

13. The multi-chambered vessel of claim 12, wherein the first component is a solid component and the second component is a liquid component.

14. The multi-chambered vessel of claim 13, wherein the solid component is a pharmaceutical formulation comprising an active pharmaceutical agent and the liquid component is a diluent.

15. The multi-chambered vessel of claim 1, wherein the multi-chambered vessel is a syringe.

16. The multi-chambered vessel of claim 1, wherein the through hole (114) comprises a first portion (302) and a second portion (304) and the plug (115) comprises a first portion (306) and a second portion (308), wherein the first portion (306) of the plug (115) is capable of being at least partially received within the first portion (302) of the through hole (114) but is not capable of being received within the second portion (304) of the through hole (114), and wherein the second portion (308) of the plug (115) is not capable of being received within the first portion (302) of the through hole (114).

17. A method of contacting a first component contained within the first chamber (102) of the multi-chambered vessel of claim 1 with a second component contained within the second chamber (104) of the multi-chambered vessel and separated from the first component by the seal (106) of the multi-chambered vessel, the method comprising disengaging the first member (106a) and the second member (106b) thereby opening the channel between the first chamber (102) and the second chamber (104) such that the first component and the second component can contact one another.

18. A method of dispensing multiple components or multiple doses of one or more components from the multi-chambered vessel according to claim 1, wherein a first component or first dose of the multiple components or multiple doses is contained within the first chamber (102) of the multi-chambered vessel and a second component or second dose of the multi-chamber vessel, the first component or first dose being separated from the (104) of the multi-chambered vessel, the first component or first dose being separated from the second component or second dose by the seal (106), the method comprising:
   (i) dispensing the first component or first dose from the multi-chambered vessel via a first outlet,
   (ii) causing the first member (106a) and the second member (106b) to disengage one another by actuating the actuator thereby opening the channel between the first chamber (102) and the second chamber (104) and allowing the second component or second dose to enter the first chamber (102) via the channel,
   (iii) dispensing the second component or second dose from the multi-chambered vessel via a second outlet, wherein the first and the second outlets are the same outlet or are different outlets.

19. A kit comprising an accessory for a vessel, the accessory comprising a seal (106) comprising a first member (106a) and a second member (106b), wherein the first member (106a) and the second member (106b) are engageable with one another to form a barrier separating a first chamber (102) and a second chamber (104) in the vessel, wherein the second member (106*b*) comprises a plug (115) and the first member (106*a*) comprises a seal portion (112) and a through hole (114), the through hole (114) being configured to receive at least a portion of the plug (115) when the first member (106*a*) and the second member (106*b*) are engaged, and wherein the second member (106*b*) comprises a support structure (116) configured to engage an internal wall of the vessel and hold the plug (115) in position relative to the through hole (114) of the first member (106*a*), wherein the first member (106*a*) has a greater resistance to pressure exerted in a distal direction via an actuator of the vessel than the second member (106*b*).

20. The kit of claim 19, further comprising securing means for securing the first member (106*a*) or the second member (106*b*) to an internal wall of the vessel.

21. A method of converting a vessel having a first chamber (102) into a converted vessel, wherein the converted vessel comprises the first chamber (102) and a second chamber (104), the converted vessel being capable of controlling communication between the first chamber (102) and the second chamber (104), the method comprising inserting a seal (106) into the vessel having the first chamber (102) wherein the inserting of the seal forms the second chamber (104) within the vessel, wherein the seal (106) comprises a first member (106*a*) and a second member (106*b*), wherein the first member (106*a*) and the second member (106*b*) are engageable with one another to form a barrier separating the first chamber (102) and the second chamber (104) in the converted vessel, wherein the second member (106*b*) comprises a plug (115) and the first member (106*a*) comprises a seal portion (112) and a through hole (114), the through hole (114) being configured to receive at least a portion of the plug (115) when the first member (106*a*) and the second member (106*b*) are engaged, and wherein the second member (106*b*) comprises a support structure (116) configured to engage an internal wall of the vessel and hold the plug (115) in position relative to the through hole (114) of the first member (106*a*), wherein the first member (106*a*) has a greater resistance to pressure exerted in a distal direction via an actuator of the converted vessel than the second member (106*b*).

* * * * *